United States Patent
Lips et al.

(10) Patent No.: US 10,042,013 B2
(45) Date of Patent: Aug. 7, 2018

(54) ACTIVE POSITION MARKER SYSTEM FOR USE IN AN MRI APPARATUS

(71) Applicant: KONINKLIJKE PHILIPS N.V., Eindhoven (NL)

(72) Inventors: Oliver Lips, Eindhoven (NL); Sascha Krueger, Eindhoven (NL); Marinus Johannes Adrianus Maria Van Helvoort, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1029 days.

(21) Appl. No.: 14/378,116

(22) PCT Filed: Feb. 1, 2013

(86) PCT No.: PCT/IB2013/050849
§ 371 (c)(1),
(2) Date: Aug. 12, 2014

(87) PCT Pub. No.: WO2013/121315
PCT Pub. Date: Aug. 22, 2013

(65) Prior Publication Data
US 2015/0035533 A1 Feb. 5, 2015

Related U.S. Application Data

(60) Provisional application No. 61/598,410, filed on Feb. 14, 2012.

(30) Foreign Application Priority Data

Feb. 14, 2012 (EP) .................................... 12155301

(51) Int. Cl.
*G01V 3/00* (2006.01)
*G01R 33/28* (2006.01)
(Continued)

(52) U.S. Cl.
CPC ............ *G01R 33/287* (2013.01); *A61B 90/39* (2016.02); *A61M 25/0127* (2013.01);
(Continued)

(58) Field of Classification Search
CPC ...................................................... G01R 33/36
(Continued)

(56) References Cited

U.S. PATENT DOCUMENTS 6,087,831 A 7/2000 Boernert
6,385,482 B1 5/2002 Boksberger
(Continued)

FOREIGN PATENT DOCUMENTS

JP 2003255091 A 9/2003
WO 2006103635 A1 10/2006
(Continued)

OTHER PUBLICATIONS

O. Unal et al, "Hybrid Tracking and Visualization of Therapeutic Devices under MRI Guidance", Proc. Intl. Soc. Mag. Reson. Med. 17,2009 p. 2564.
(Continued)

*Primary Examiner* — Louis Arana

(57) ABSTRACT

An active position marker system comprising at least one active position marker (10) and a remote transceiver unit (20) for communicating with the position marker is disclosed. Basically, the position marker (10) comprises a local RF receive coil (11) for receiving MR signals which are excited in a local volume, and a parametric amplifier (14) for amplifying and upconverting the frequency of the received MR signal into at least one microwave sideband frequency signal. This microwave signal is transmitted wirelessly or wire-bound to the transceiver unit for downconverting the same and supplying it to an image processing unit of an MR imaging apparatus.

16 Claims, 1 Drawing Sheet

(51) Int. Cl.
*G01R 33/36* (2006.01)
*A61M 25/01* (2006.01)
*A61B 90/00* (2016.01)

(52) U.S. Cl.
CPC ......... *G01R 33/36* (2013.01); *G01R 33/3621* (2013.01); *A61B 2090/3954* (2016.02); *G01R 33/3692* (2013.01)

(58) Field of Classification Search
USPC ........................................ 324/316, 322, 318
See application file for complete search history.

(56) References Cited

U.S. PATENT DOCUMENTS

| | | | |
|---|---|---|---|
| 6,906,520 B2 | 6/2005 | Heid et al. | |
| 7,289,839 B2 | 10/2007 | Dimmer | |
| 7,498,940 B2 | 3/2009 | Pettus | |
| 7,518,367 B2 | 4/2009 | Renz | |
| 7,535,363 B2 | 5/2009 | Gisselberg | |
| 7,683,619 B2 | 3/2010 | Smith | |
| 7,729,742 B2 | 6/2010 | Govari | |
| 7,778,687 B2 | 8/2010 | Dimmer | |
| 8,324,901 B2 * | 12/2012 | Hulbert | G01R 33/3415 324/322 |
| 8,415,953 B2 | 4/2013 | Cork | |
| 8,421,460 B2 * | 4/2013 | Hulbert | G01R 33/3415 324/316 |
| 2002/0156365 A1 | 10/2002 | Tsekos | |
| 2003/0227289 A1 | 12/2003 | Heid | |
| 2004/0138554 A1 | 7/2004 | Dimmer | |
| 2007/0167726 A1 | 7/2007 | Unal | |
| 2010/0001728 A1 | 1/2010 | Blank | |
| 2010/0117650 A1 | 5/2010 | Cork | |
| 2010/0253349 A1 | 10/2010 | Cork | |
| 2014/0159728 A1 * | 6/2014 | Wirtz | G01R 33/287 324/322 |

FOREIGN PATENT DOCUMENTS

| | | |
|---|---|---|
| WO | 2007027827 A2 | 3/2007 |
| WO | 2008142629 A2 | 11/2008 |

OTHER PUBLICATIONS

S. Martius et al, Wireless Local Coil Signal Transmission Using a Parametric Upconverter, Proc. Intl. Soc. Mag. Reson. Med. 17, 2009 vol. 4, p. 2934.

O. Heid et al, Cutting the Cord—Wireless Coils for MRI, Proc.Intl. Soc. Mag. Reson. Med. 17, 2009 vol. 4 p. 100.

Qian, C. et al "Integrated Detection, Amplification and Wireless Transmission of MRI Signals using a Parametric Amplifier" Proceedings of the International Society for Magnetic Resonance in Medicine, 2011.

* cited by examiner

ACTIVE POSITION MARKER SYSTEM FOR USE IN AN MRI APPARATUS

CROSS-REFERENCE TO PRIOR APPLICATIONS

This application is the U.S. National Phase application under 35 U.S.C. § 371 of International Application No. PCT/IB2013/050849, filed on Feb. 1, 2013, which claims the benefit of U.S. Provisional Patent Application No. 61/598,410, filed on Feb. 14, 2012 and European Patent Application No.12155301.0, filed on Feb. 14, 2012. These applications are hereby incorporated by reference herein.

FIELD OF THE INVENTION

The invention relates to an active position marker system comprising at least one active position marker and a remote transceiver unit for communicating with the at least one position marker, for use in an MR imaging apparatus. A position marker is considered "active" in the sense, that it is provided for receiving MR signals substantially only from a local volume after RF excitation of the local volume which volume at least substantially surrounds or which is at least substantially surrounded by the marker or adjacent to the marker, so that on the basis of these "local" MR signals the position of the marker can be determined and/or imaged by means of an MR imaging apparatus especially in an MR image of an examination object with a desired accuracy.

Further, the invention relates to a medical device in the form of an interventional or non-interventional instrument like a catheter, a surgical device, a biopsy needle, a pointer or another invasive or non-invasive device, as well as an RF surface coil, an RF pad coil, an RF head coil, a stereotactic frame or any other instrument which can be used during an MR image generation, which medical device comprises such an active position marker as a built-in unit, in order to determine and/or make visible its position in an MR image of an examination object.

BACKGROUND OF THE INVENTION

As generally known, in an MR imaging (MRI) system or MR scanner, an examination object, usually a patient, is exposed to a uniform main magnetic field ($B_0$ field) so that the magnetic moments of the nuclei within the examination object form a certain net magnetization of all nuclei parallel to the $B_0$ field, which can be tilted leading to a rotation around the axis of the applied $B_0$ field (Larmor precession). The rate of precession is called Larmor frequency which is dependent on the specific physical characteristics of the involved nuclei, namely their gyromagnetic ratio, and the strength of the applied $B_0$ field. The gyromagnetic ratio is the ratio between the magnetic moment and the spin of a nucleus.

By transmitting an RF excitation pulse ($B_1$ field) which is orthogonal to the $B_0$ field, generated by means of an RF transmit antenna or coil, and matching the Larmor frequency of the nuclei of interest, the spins of the nuclei are excited and brought into phase, and a deflection of their net magnetization from the direction of the $B_0$ field is obtained, so that a transversal component in relation to the longitudinal component of the net magnetization is generated.

After termination of the RF excitation pulse, the relaxation processes of the longitudinal and transversal components of the net magnetization begin, until the net magnetization has returned to its equilibrium state, wherein T1 and T2 is the time required for the longitudinal and transversal magnetization, respectively, to return to 63% of its equilibrium value. MR signals which are generated by the precessing magnetization, are detected by means of an RF receive antenna or coil. The received MR signals which are time-based amplitude signals, are then Fourier transformed to frequency-based MR spectrum signals and processed for generating an MR image of the nuclei of interest within an examination object.

In order to obtain a spatial selection of a slice or volume within the examination object and a spatial encoding of the received MR signals emanating from a slice or volume of interest, gradient magnetic fields are superimposed on the $B_0$ field, having the same direction as the $B_0$ field, but having gradients in the orthogonal x-, y- and z-directions. Due to the fact that the Larmor frequency is dependent on the strength of the magnetic field which is imposed on the nuclei, the Larmor frequency of the nuclei accordingly decreases along and with the decreasing gradient (and vice versa) of the total, superimposed $B_0$ field, so that by appropriately tuning the frequency of the transmitted RF excitation pulse (and by accordingly tuning the resonance frequency of the RF/MR receive antenna), and by accordingly controlling the gradient magnetic fields, a selection of nuclei within a slice at a certain location along each gradient in the x-, y- and z-direction, and by this, in total, within a certain voxel of the object can be obtained.

Medical instruments or devices especially in the form of interventional and non-interventional instruments, tools and other as mentioned above are frequently used during the examination or treatment of an examination object and especially of a local zone or area thereof by means of an MR imaging apparatus. Such medical instruments or devices are for example pacemakers, catheters, biopsy needles, surgical devices, pointers and other which are used for example for biopsies, thermal ablations, brachytherapy, slice selection and other invasive or non-invasive purposes as mentioned above. Further, RF surface coils, RF pad coils, RF head coils, stereotactic frames and other non-interventional instruments are also used during MR imaging. For all these and other examinations it is important to precisely position the instrument and especially a certain part or property thereof (like its tip or axis) at a certain desired location at or within the examination object. This requires that during the positioning of the instrument by an operator, the current position of the instrument or an interesting part thereof, especially its tip, is precisely determined and imaged or indicated in the MR image of the related examination object, so that a desired destination at or within the examination object can be reached.

For this purpose, the above instruments or medical devices can be equipped with a position marker having a local RF coil, the position of which can be imaged by means of an MR imaging apparatus in the MR image of the related examination object.

A desired spot-like indication of the position and by this a desired accuracy of the position indication can be obtained either by dimensioning the local RF coil such small that it receives ("local") MR signals substantially only (but with a sufficient MR signal strength) from an accordingly small or spot-like local volume of the examination object, and/or by providing a small or spot-like local volume in the form of a marker material (e.g. $^{19}F$, $^{13}C$, $^{23}Na$ or other) having a gyromagnetic ratio and accordingly a Larmor frequency which is different from the gyromagnetic ratio and the Larmor frequency of the material of the examination object (usually water and fat), so that upon RF excitation of this local volume only, the excited ("local") MR signals provide a spot-like signal source which can be imaged in an MR image of an examination object. In the latter case, more in detail, by a first RF pulse sequence the position data of the marker material is determined and by a second RF pulse sequence the image data of the examination object is determined, and then both data sets are displayed in the form of a common MR image.

Generally, two different types of such position markers can be distinguished, namely active and passive markers. Active markers as defined above usually comprise a sensor especially in the form of a local RF coil for receiving the said local MR signals emitted from a local volume, wherein these local MR signals are conveyed by means of a cable to a remote MR receiver of an MR imaging apparatus in order to determine and/or image the position of the local volume and by this the position of the marker on the basis of the received local MR signal as explained above.

In contrast to this, passive markers are usually imaged in an MR image for example by distorting, enhancing or modifying due to their physical properties or due to an own (intrinsic) RF resonance (which is excited by the applied external RF excitation field), the $B_0$ field or the RF excitation field transmitted by the MR imaging apparatus and by this the MR signals emitted by the examination object.

All these principles enable a position determination and visualization of the active (and passive) marker, respectively, in connection with the applied gradient magnet fields within the MR image of an examination object as explained above.

However, one major drawback of the above active markers and of interventional or non-interventional instruments comprising such an active marker is, that an RF cable connection is required for feeding the received MR signals from the active marker to a remote MR receiver or MR imaging apparatus. On the one hand, such a cable reduces the comfort and ease of use and introduces mechanical safety risks, especially in case of an interventional instrument, limits the flexibility of handling, and increases the time needed to prepare an MR imaging procedure. On the other hand, a (metallic) cable for connecting the active position marker with an MR receiver usually has to be guided inside and through an examination space of an MR imaging apparatus, so that it poses a potential safety risk due to resonant common mode currents which are induced on the cable by the RF excitation field emitted by the related RF transmit antenna of the MR imaging apparatus.

WO 2006/103635 discloses an interventional device which is connected by means of a cable to a remote spectrometer, for conducting an informative signal from the interventional device to the spectrometer. Common mode resonances on the cable are avoided by subdividing the cable into a plurality of capacitively coupled portions of the cable. The resulting attenuation of the informative signal is compensated by amplifying the signal by means of a parametric amplifier included into the interventional device, wherein a pump signal is supplied from the spectrometer to the parametric amplifier over the cable for converting the frequency of the informative signal to a higher frequency which is subject to a lower attenuation on the cable.

SUMMARY OF THE INVENTION

One object underlying the invention is to remove the above mentioned drawbacks of an active position marker and to provide an active position marker in a simple manner such that it can be handled easily and flexibly without imposing the above safety risks.

This object is solved by an active position marker according to claim 1, especially in combination with a transceiver unit according to claim 9, and by an active position marker system according to claim 13.

An advantage of using a parametric amplifier for amplifying the received MR signal and frequency-upconverting this signal is that it can be conducted with a very low noise. Further, it can be realized by a very simple circuit structure in a cost effective manner, also due to the fact, that the requirements as to dynamic range, linearity, synchronization and other parameters of the transmission of an MR signal which is used for position determination or tracking purposes have been revealed to be not so high as in case of an MR signal which is used for MR image generation of an examination object.

An advantage of the transmission of the MR signal especially in an upconverted microwave frequency band is, that in case of using a cable for connecting the active position marker with the remote transceiver unit, such a cable can be realized in the form of a microwave cable having a very small diameter. Possible RF common mode currents on the microwave cable can be reduced or avoided in a comparatively simple manner by including capacitors serially into the cable as generally known from the WO 2006/103635 above, wherein the transmission of the upconverted MR signal along the cable is not substantially attenuated by such capacitors.

Another advantage of the above (wireless) transmission of electromagnetic waves in comparison to optical tracking techniques consists in the fact, that the basic principle of operation of the position marker is not changed, i.e. it stays an MR based technique. Thus, the integration of the position marker into a usual MR imaging sequence and the data handling can be easily managed. Furthermore, all existing methods and applications can still be used.

The active position marker can be provided as a separate (stand-alone) unit for attaching it at an interventional or a non-interventional instrument or at an examination object in order to determine and/or image a position or motion of the instrument or the examination object, respectively, wherein the transceiver unit is preferably arranged remotely from the position marker, either again as a stand-alone unit which is connected via a standard interface with an MR receiver, or is integrated into an MR receiver or an MR imaging apparatus.

The dependent claims disclose advantageous embodiments of the invention.

It will be appreciated that features of the invention are susceptible to being combined in any combination without departing from the scope of the invention as defined by the accompanying claims.

Further details, features and advantages of the invention will become apparent from the following description of preferred and exemplary embodiments of the invention which are given with reference to the drawings.

DETAILED DESCRIPTION OF EMBODIMENTS

Figure 1:
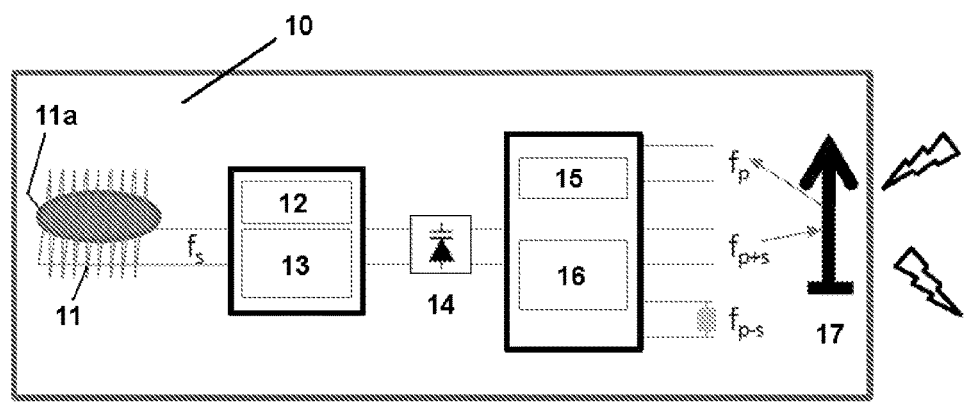
FIG. 1 shows a schematic block diagram of an active position marker according to an embodiment of the invention.
Figure 2:
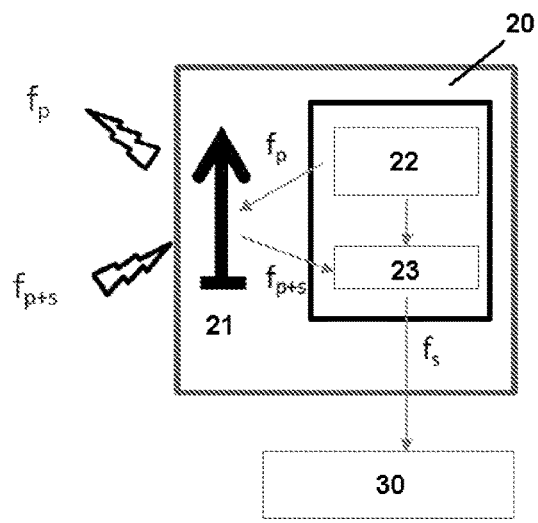
FIG. 2 shows a schematic block diagram of a remote transceiver unit according to an embodiment of the invention.

FIGS. 1 and 2 together show a schematic block diagram of the components of an active position marker system according to a first embodiment of the invention. Basically, the position marker system comprises at least one active position marker 10 according to FIG. 1 for receiving, amplifying, frequency-upconverting and transmitting local MR signals, and a remote transceiver unit 20 according to FIG. 2 for receiving and frequency-downconverting the transmitted local MR signals and for supplying these signals to an image processing unit 30 of an MR imaging apparatus.

According to the first embodiment, the transmission is conducted wirelessly and preferably in the microwave frequency range between about 1 and about 300 GHz, like e.g. in the 2.4 GHz band or another one of the ISM frequency bands like 24 GHz, 61 GHz, 122 GHz or 244 GHz etc. However, in principle also frequencies below the microwave frequency range, but substantially higher than the MR frequency might be used (e.g. between about 400 MHz, especially 500 MHz, and about 1 GHz). This can be advantageous if e.g. a significant penetration or transmission of the transmitted signals into/within an examination object like a human body is needed (e.g. in case of interventional instruments). The explanations in the following which refer to a transmission in the microwave frequency range are applicable to a transmission in the frequency range between about 400 MHz and about 1 GHz accordingly.

Basically, the active position marker 10 comprises an RF sensor, especially in the form of a local RF coil 11, which encloses or is surrounded by a local volume 11a, preferably in the form of a marker material (signal source), for receiving a local MR signal excited in the local volume as explained above, a parametric amplifier 14 comprising a non-linear reactance, and at least one first antenna 17. Preferably, a first filter 12 and a first matching network 13 is connected between the RF receive coil 11 and the parametric amplifier 14. Further, preferably a second filter 15 and a second matching network 16 is connected between the parametric amplifier 14 and the at least one first antenna 17.

Basically, the transceiver unit 20 comprises at least one second antenna 21, preferably a pump frequency signal generator 22, and a demodulator 23, the output of the latter is connected with a conventional image processing unit 30 of an MR imaging apparatus.

Alternatively, instead of the transceiver unit 20, the active position marker 10 can comprises a pump frequency signal generator, wherein in this case, it is preferred that the pump frequency signal is transmitted from the active position marker 10 to the transceiver unit 20 for frequency-downconverting the received local MR signal by means of the demodulator (23).

More in detail, the local RF coil 11 is as generally known and explained above dimensioned such small that it receives MR signals substantially only from the said local volume, so that the location information which is determined from the MR signal fs is sufficiently exact for determining and imaging the position of the local RF coil 11 in an MR image. Accordingly, a local volume of a marker material (if provided) is dimensioned as explained above to be such small that its position (and by this the position of the local RF coil 11 and by this of the position marker 10) can be determined or imaged substantially with a spot-like extension which is small enough for obtaining a desired localization accuracy in the MR image of an examination object, but large enough that the MR signals which are received from the local volume enable a determination of the position of the local RF coil 11 and by this of the position marker.

The local RF receive coil 11 can be realized e.g. in the form of a solenoid coil or a toroid coil, wherein the latter has the advantage that the received RF signal strength is less dependent on the orientation of the (toroid) coil than in case of a solenoid coil.

Further, the local RF receive coil 11 is dimensioned such that it can be tuned to be resonant at the related Larmor frequency of the material within the local volume as generally known, wherein the local RF receive coil 11 is preferably connected together with a resonance capacitor into a tunable resonant circuit as generally known.

The local volume 11a can be provided by a volume of material of the examination object but preferably comprises a marker material having a gyromagnetic ratio and accordingly a Larmor frequency which is different from the gyromagnetic ratio and by this from the Larmor frequency of the material of the examination object (usually water and/or fat) as explained above. The marker material is preferably included in a small vessel and can be e.g. $^{19}F$ (or $^{13}C$, $^{23}Na$ or other) or, more general, water with an agent for shortening or lengthening especially the T1 relaxation time in comparison to the T1 relaxation time of the material of the examination object.

The (local) MR signal fs which is induced in the local RF receive coil 11 is preferably bandpass-filtered by the first filter 12 and applied preferably via the first impedance matching network 13 to the input of the parametric amplifier 14.

The parametric amplifier 14 substantially comprises a non-linear reactance, realized by means of a non-linear inductor or a non-linear capacitor, preferably a varactor diode, wherein the value of the non-linear reactance is varied periodically by means of an applied pump frequency signal fp having a frequency in one of the above mentioned frequency ranges for transmission, so that the applied MR signal fs is amplified through non-linear signal mixing and frequency-upconverted as generally known into upper and lower sideband frequency signals having the frequencies: n*fp+/−m*fs.

Preferably, a bias voltage source (not indicated) is provided for adjusting a bias point of the varactor diode as generally known.

Of course also other embodiments of parametric amplifiers can be used.

Preferably, at least one of the two first order upper and lower sideband frequency signals fp+fs, fp−fs, is selected and transmitted wirelessly by means of the first antenna 17 to the transceiver unit 20.

In order to select at least one upper and/or at least one lower sideband frequency signal, for example the upper sideband frequency signal fp+fs, and for terminating or short-circuiting the other sideband frequency signals, the second filter 15 is accordingly dimensioned as a bandpass filter for this sideband frequency and is connected between the output of the amplifier 14 and the first antenna 17. Further, for impedance matching the output of the parametric amplifier 14 or of the second filter 15, respectively, to the first antenna 17, preferably the second matching network 16 is connected between the parametric amplifier 14 or second filter 15, respectively, and the first antenna 17.

The selected sideband of the frequency-upconverted MR signal is then transmitted wirelessly by means of the first antenna 17 to the transceiver unit 20, where it is received by means of the second antenna 21 and fed to the demodulator 23.

In the demodulator 23, the received sideband of the frequency-upconverted MR signal is downconverted to the frequency of the original MR signal by means of the pump frequency signal fp which is generated by the pump signal generator 22 and supplied to the demodulator 23. From the output of the demodulator 23, the downconverted (i.e. original) MR signal is submitted to a conventional image processing unit 30 of an MR imaging apparatus for position determination and image generation of the RF receive coil 11.

Further, the pump frequency signal fp is also applied at the second antenna 21 and transmitted wirelessly by means of this antenna 21 to the active position marker 10 where it is received by the first antenna 17.

In the active position marker 10, the pump frequency signal fp is applied preferably via the second filter 15 and preferably via the second impedance matching network 16 to the parametric amplifier 14 for amplifying and frequency-upconverting the local MR signal fs which is received by means of the local RF receive coil 11 and applied to the amplifier 14 as mentioned above.

For this purpose, the optional second filter 15 is dimensioned for bandpass filtering the received pump frequency signal fp, and the optional second matching network 16 is dimensioned for impedance matching the first antenna 17 to the second filter 15 or the parametric amplifier 14, respectively.

In case that both the at least one transmitted sideband frequency signal fp+/−fs and the received pump frequency signal fp shall be bandpass-filtered and impedance-matched, preferably each an own individual second filter and an own individual second matching network is provided for both signals, which are each dimensioned for the related sideband frequency and the pump frequency, respectively.

The first and the second filter 12, 15 and the first and the second matching network 13, 16 can be realized by lumped elements or implemented as transmission line circuits as generally know.

For improving the reliability of the wireless connection between the active position marker 10 and the transceiver unit 20, more than one first and/or more than one second antenna 17, 21 can be used at the active position marker 10 and/or at the transceiver unit 20, respectively, which are preferably operated according to the known MIMO (multiple input, multiple output) principles.

Further, the reliability of transmission of the local MR signal to the transceiver unit 20 can also be improved by transmitting more than one of the frequency-upconverted sideband signals (e.g. the first order upper and the first order lower sideband frequency signal fp+fs, fp−fs) simultaneously, preferably by means of each one first antenna for each sideband signal. These sideband signals are preferably received by means of each one second antenna for each sideband frequency and downconverted in parallel in order to select for the further image processing the one of the received local MR signals which has the highest signal strength or the highest signal to noise ratio.

Further, for distinguishing two or more active position markers 10 which are used at the same time, each one of different sideband frequencies fp+fs, fp−fs, n*fp+m*fs, . . . can be used and transmitted by each one of the active position markers 10, and/or pump signals having different frequencies can be generated and transmitted by the transceiver unit 20, so that on the basis of the frequency of the upconverted sideband signals which are received by the transceiver unit 20, each of the active position markers 10 can be identified. For this purpose, for example a related look-up table is stored in the transceiver unit 20 indicating the related frequency of each active position marker, so that each an identification signal designating each one active position marker can be generated and submitted together with the related received MR signal to the image processing unit 30. Accordingly, the first and the second filters and matching networks 12, 13; 15, 16 in the active position markers 10 are dimensioned according to the assigned pump frequency and/or sideband frequency.

As an example, a frequency of a pump signal fp of 2.4 GHz is assumed which is generated by means of the pump signal generator 22 of the transceiver unit 20 and transmitted by means of the second antenna 21 to the first antenna 17. The received pump frequency signal fp is fed preferably via the second filter 15 and the second matching network 16 as explained above to the parametric amplifier 14, where it is mixed with the local MR signal of 128 MHz received by the local RF receive coil 11, so that a frequency-upconverted lower sideband signal of 2.272 GHz and a frequency-upconverted upper sideband signal of 2.528 GHz is created. Whereas e.g. the lower sideband signal is open- or short-circuited or terminated with an impedance, the upper sideband signal is fed preferably via the second filter 15 and the second matching network 16 to the first antenna 17 and transmitted to the transceiver unit 20 for downconverting the same by means of the demodulator 23 as explained above. The downconverted local MR signal is supplied to an image processing unit 30 of an MR imaging apparatus for determining and imaging the position of the local RF receive coil 11 of the active position marker 10 in an MR image of an examination object as explained above. For improving the reliability of the MR signal transmission, both sideband signals can be transmitted, downconverted and selected for image processing as explained above.

The transceiver unit 20 may either be realized as an additional device as indicated in FIG. 2, or it may be implemented into an MR imaging system. In the first case, it is connected with the MR imaging system via a standard interface preferably in the same way as a standard MR receive coil for receiving MR signals of an examination object.

An active position marker system according to a second embodiment of the invention differs from the above first embodiment in that instead of a wireless connection, a first cable interface is provided at the active position marker 10 and a second cable interface is provided at the remote transceiver unit 20, for connecting both with each other by means of a cable, wherein the at least one first and second antenna 17, 21 can be omitted. At least one of the cable interfaces can be realized in the form of a plug-connector for connecting and disconnecting a cable at the active position marker and/or at the transceiver unit, and/or at least one of the cable interfaces is realized in the form of a fixed cable connection which cannot be disconnected from the active position marker and/or from the transceiver unit.

Preferably, the transmission is conducted in the above microwave frequency range because in this case the suppression of common mode currents on a microwave cable can be realized much easier and in smaller size (e.g. as disclosed in the above WO 2006/103635), so that it can be handled much more flexible, than in case of a common cable for the MR frequency range which requires trap circuits and transformers integrated into the cable. On the other hand, the loss of a (microwave) cable generally increases with increasing frequency, so that the case may be that a transmission via a cable at frequencies below the microwave frequency range (e.g. between about 400 MHz, especially 500 MHz, and about 1 GHz as indicated) above is preferred. Apart from this, the explanations with reference to the first embodiment also apply for the second embodiment of the invention.

The active position marker 10 can be arranged at a medical device especially in the form of an interventional or non-interventional instrument (not shown) at a location of this instrument, which is the interesting part to be imaged, for example its tip, which is to be guided to a certain desired destination area at or within an examination object.

In case of using the active position marker 10 as a stand-alone unit, it can also be positioned e.g. at an examination object in order to detect (and compensate by means of the image processing unit) any undesired motion of the examination object.

Further, the active position marker 10 can be used e.g. for MR guided biopsies (e.g. for defining a scan plane if it is arranged in a needle holder) or for tracking of interventional devices or RF transmit/receive coils in the form of surface coils and many other purposes.

While the invention has been illustrated and described in detail in the drawings and foregoing description, such illustration and description are to be considered illustrative or exemplary and not restrictive, and the invention is not limited to the disclosed embodiments. Variations to embodiments of the invention described in the foregoing are possible without departing from the scope of the invention as defined by the accompanying claims.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. An active position marker, comprising:
   a local RF receive coil for receiving local MR signals, which are excited in a local volume, which is surrounded by and/or surrounds the local RF receive coil;
   a parametric amplifier provided in the active position marker, the parametric amplifier being configured to amplify the received local MR signal and for upconverting its frequency via a pump frequency signal into at least one upper and/or at least one lower sideband frequency signal;
   an antenna, provided in the active position marker for wirelessly transmitting, or a cable interface for wirebound transmitting, the at least one upper and/or at least one lower sideband frequency signal of the frequency-upconverted local MR signal; and
   a filter configured to bandpass filter the received local MR signal, the filter being connected between the local RF receive coil and the parametric amplifier.

2. The active position marker according to claim 1, wherein a local volume of the active position marker comprises a marker material.

3. The active position marker according to claim 1, further comprising a matching network is connected between the local RF receive coil and the parametric amplifier, the matching network being configured to match an impedance of the parametric amplifier to an impedance of the local RF receive coil.

4. The active position marker according to claim 3, wherein the match network is a first matching network, and the active position marker further comprises a second matching network connected between the parametric amplifier and the antenna, or the cable interface, respectively, for impedance-matching the amplifier to the antenna, or to the cable interface, respectively.

5. The active position marker according to claim 1, wherein the filter is a first filter, and the active position marker further comprises second filter connected between the parametric amplifier and the antenna, or the cable interface, respectively, for bandpass filtering the at least one upper sideband signal and/or the at least one lower sideband signal of the frequency-upconverted MR signal.

6. A medical device, comprising an active position marker according to claim 1, the medical device being an interventional or non-interventional instrument.

7. The medical device according to claim 6, wherein the medical device is one of: a pacemaker, a catheter, a surgical device, a biopsy needle, a pointer, an RF transmit and/or receive surface coil, an RF pad coil, an RF head coil, or a stereotactic frame.

8. An active position marker system comprising at least one active position marker according to claim 1, and a remote transceiver unit.

9. The active position marker system according to claim 8, comprising a plurality of active position markers which are each operated by means of each one of a plurality of pump signals each having one of different pump frequencies, and/or which transmit each one of a plurality of upper and/or lower sideband frequency signals each having one of different upper and/or lower sideband frequencies, wherein the remote transceiver unit comprises a look-up table for assigning each active position marker a unique identification on a basis of a frequency of the received frequency-upconverted MR signal, wherein the unique identification is fed together with an downconverted MR signal to an image processing unit of an MR imaging system.

10. The active position marker according to claim 1, wherein the local RF receive coil encloses or is surrounded by the local volume.

11. An active position marker, comprising:
    a local RF receive coil for receiving local MR signals, which are excited in a local volume, which is surrounded by and/or surrounds the local RF receive coil;
    a parametric amplifier provided in the active position marker, the parametric amplifier being configured to amplify the received local MR signal and for upconverting its frequency via a pump frequency signal into at least one upper and/or at least one lower sideband frequency signal; and
    an antenna, provided in the active position marker for wirelessly transmitting, or a cable interface for wirebound transmitting, the at least one upper and/or at least one lower sideband frequency signal of the frequency-upconverted local MR signal.

12. The active position marker according to claim 11, wherein a local volume of the active position marker comprises a marker material.

13. The active position marker according to claim 11, further comprising a matching network is connected between the local RF receive coil and the parametric amplifier, the matching network being configured to match an impedance of the parametric amplifier to an impedance of the local RF receive coil.

14. The active position marker according to claim 13, wherein the matching network is a first matching network, and the active position marker further comprises a second matching network connected between the parametric amplifier and the antenna, or the cable interface, respectively, for impedance-matching the amplifier to the antenna, or to the cable interface, respectively.

15. A medical device, comprising an active position marker according to claim 11, the medical device being an interventional or non-interventional instrument.

16. The medical device according to claim 15, wherein the medical device is one of: a pacemaker, a catheter, a surgical device, a biopsy needle, a pointer, an RF transmit and/or receive surface coil, an RF pad coil, an RF head coil, or a stereotactic frame.

* * * * *